United States Patent [19]

Friend et al.

[11] Patent Number: 4,962,905

[45] Date of Patent: Oct. 16, 1990

[54] APPARATUS FOR HOLDING SAMPLES DURING SOLDERABILITY TESTING

[75] Inventors: Frank H. Friend, Southampton, Pa.; Kon-Mang Lin, Pennington, N.J.

[73] Assignee: AT&T Bell Laboratories, Murray Hill, N.J.

[21] Appl. No.: 373,559

[22] Filed: Jun. 30, 1989

[51] Int. Cl.$^5$ ............................................. B23K 37/00
[52] U.S. Cl. ................................ 248/125; 248/316.1; 228/104; 73/865.8
[58] Field of Search ............... 248/669, 62, 74.1, 74.4, 248/125, 132, 324, 316.5, 231.5, 316.1; 24/509, 510; 269/254 R, 238, 246; 73/304 R, 856, 865.8; 228/104, 259, 39

[56]  References Cited

U.S. PATENT DOCUMENTS

| | | | |
|---|---|---|---|
| 2,038,043 | 4/1936 | Hasselblad | 248/316.5 |
| 2,454,857 | 11/1948 | Bish | 24/510 |
| 2,964,007 | 12/1960 | Buffington | 228/39 |
| 3,312,434 | 4/1967 | Simon | 248/316.5 |
| 3,612,456 | 10/1971 | Palmer | 248/125 |
| 3,914,828 | 10/1975 | Noda | 24/510 |
| 4,411,050 | 10/1983 | Couture | 24/510 |

FOREIGN PATENT DOCUMENTS 642314  5/1928  France ............................... 248/316.5

Primary Examiner—Ramon O. Ramirez
Assistant Examiner—Robert A. Olson
Attorney, Agent, or Firm—Robert B. Levy

[57] ABSTRACT

A sample holder (22) is provided for use with a solderability testing machine (10) to releasably engage a sample 12) for immersion into a solder bath (26). The sample holder comprises a beam (28) provided at its upper end (30) with means (29) for engaging the solderability tester. A clamping mechanism (34) is carried by the beam (28) below its upper end for releasably holding the sample. The beam also carries a threaded, depth-controlling member (50) which may be threadedly adjusted to precisely control the depth of immersion of the sample held by the holder into the sample bath.

11 Claims, 4 Drawing Sheets

APPARATUS FOR HOLDING SAMPLES DURING SOLDERABILITY TESTING

TECHNICAL FIELD

This invention generally relates to an apparatus for holding an electronic component, or a piece of circuit board, during solderability testing.

BACKGROUND OF THE INVENTION

At the present time, soldering remains the preferred method for attaching each conductive member (e.g., a lead or termination) of an electronic component to a corresponding metallized region on a printed circuit board. Currently, there is a trend towards smaller electronic components which have reduced-size conductive members and a corresponding reduction in the size of the metallized regions on the printed circuit board to which such conductive members are soldered. Reducing the size of the component's conductive members and the size of the metallized regions on the circuit board reduces the area of contact between each conductive member and the circuit board, making it increasingly necessary to achieve a high-quality solder joint between them.

An important criterion in achieving a high-quality solder joint between each conductive member of the component and the corresponding metallized region on the circuit board is the solderability of the conductive member and metallized region. The solderability of the conductive members of the component and the metallized region on the circuit board is determined by the extent to which solder "wets" them (i.e., the extent to which the solder adheres to them). For this reason, sample lots of components and circuit boards are commonly tested to determine their solderability.

In the past, the solderability of sample lots of components and printed circuit boards (collectively referred to as "samples") has been evaluated by fluxing the samples and then immersing them in a bath of molten solder. After immersion, the sample is withdrawn and then visually inspected to determine the extent to which solder has wetted it. As may be appreciated, this technique for evaluating solderability is highly subjective and offers no accurate mechanism for discerning small variations in the solderability of identical samples.

Recently, testers have been developed for objectively measuring solderability in accordance with the wetting force of solder on the sample. Upon immersion of the fluxed sample into the molten solder bath, the solder wets the metallic portions of the sample (e.g., the leads of the component or the metallized regions on the printed circuit board). As the solder wets the metallic portions of the sample, the sample is subjected to a wetting force which overcomes the buoyancy force opposing immersion of the sample into the bath. By the same token, the wetting force of the solder on the sample increases the amount of force required to withdraw the sample once it has been immersed. By measuring the wetting force on the sample during immersion into, and withdrawal from, the solder bath, an accurate measure of the solderability of the sample can be obtained.

Present day solderability testers typically employ a linear variable differential transformer (LVDT) to measure the wetting force of solder on a sample. In practice, an "alligator"-type clip is used to secure the sample to the LVDT so that the sample overlies a bath of molten solder held in a heated pot. The pot is driven upwards and downwards to and from the sample by a stepper motor so that the sample can be immersed into, and withdrawn from, the solder bath. As the sample is immersed into, and withdrawn from, the solder path, the LVDT measures the wetting force on the sample, thereby providing an indication of its solderability.

A disadvantage of the above-described solderability testers is that the alligator clip used to secure the sample to the LVDT usually cannot accommodate very small samples, such as discrete surface-mounted resistors and capacitors. Further, the prior art alligator clip, by its very design, often contributes to inaccurate solderability measurement as a result of its inability to hold certain types of samples such that only a limited part of its metallic portion is immersed into a bath of solder in a vertical manner. Depending on the geometry of the sample, only a small part of its metallic portion is ultimately soldered during assembly. This is particularly true with those surface-mounted electronic components which have an arcuate toe at the lowermost end of their conductive members. Only the lower portion of the toe is ultimately soldered to a metallized region on the circuit board. Since only the lower portion of the toe, especially its bottom surface, is ultimately soldered, its solderability (rather than the solderability of the rest of the conductive member) is really of concern. With the prior art alligator clip, it is usually impossible to hold the sample so that only the toe of the conductive member may be immersed to obtain an exact solderability measurement.

Thus, there is a need for an improved clip or holder for securing a component or printed circuit board during solderability testing.

SUMMARY OF THE INVENTION

The present invention is directed to a family of sample holders, each adapted for mounting to a solderability tester, for holding a sample having a metallic portion so that the tester can immerse part of the metallic portion of the sample in a solder bath to determine its solderability. Each sample holder comprises a longitudinal beam having means at one end thereof adapted to engage the solderability tester. Near the end of the beam opposite the engaging means is a clamping mechanism for engaging the sample. The clamping mechanism of each sample holder of the family is adapted to engage one or more particular classes of samples. For example, one sample holder of the family is provided with a clamping mechanism designed to engage either a piece of printed circuit board or a plastic leaded chip carrier so that its metallic portion is held at a predetermined angle relative to the beam to limit the exposure of the metallic portion upon immersion. Another of the family of sample holders is provided with a clamping mechanism designed to engage small discrete components.

Each sample holder of the family has a horizontal projection extending outwardly opposite the clamping mechanism. An immersion depth-controlling member, which has a very fine wire depending therefrom, is theaded vertically through the projection so that the wire extends below the holder. By varying the extent to which the depth-controlling member is threaded through the projection, the height of the depth-controlling member from the top of the solder bath can be precisely established. In this way, the depth of immersion of the metallic portion of the sample can be controlled. Also, each of the sample holders has a pair of dished arms extending out from the beam in horizontal, spaced-apart parallelism above the clamp for carrying a calibration weight placed thereon to calibrate the solderability testing machine prior to operation.

An important attribute of each sample holder in the family of sample holders of the present invention is that each is designed to remain balanced, (i.e., the sample holder's beam remains vertical) while the sample is engaged by it. This assures that the solderability tester remains balanced, allowing for more accurate solderability measurements.

DETAILED DESCRIPTION

Figure 1:
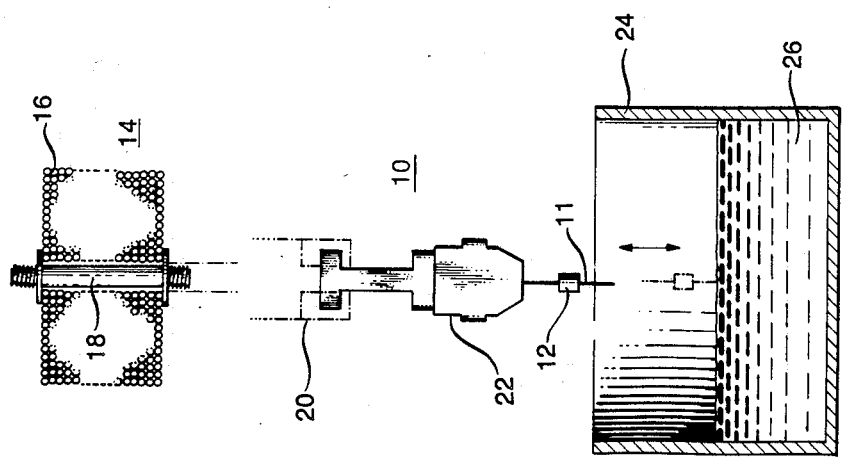
FIG. 1 is a front view, in cross section, of a solderability tester according to the prior art.

FIG. 1 is a front view, in cross-section, of a prior art solderability tester 10, of the type commercially available, for testing the solderability of a metallic portion 11 (i.e., a conductive member) on a sample 12, typically an electronic component. The tester 10 includes a force-sensing mechanism 14 in the form of a linear variable differential transformer (LVDT) comprised of an annular winding 16 rigidly secured to a support (not shown). A spring-biased magnetic core 18 is mounted for reciprocal movement in a vertical direction through the center of the winding 16. When the winding 16 is electrically energized, vertical movement of the core 18 through it causes a change in the signal in the winding, the extent of the change in the signal depending on the extent of the core movement.

The core 18 depends below the winding 16 and is provided with a hanger 20 at its lower end (typically taking the form of a strip of metal having a pair of spaced-apart tabs at its lower end, each bent in a "U" shape) for engaging a sample holder 22. The sample holder 22 is adapted to hold the sample 12, which has been fluxed, so that the fluxed sample may be immersed into, and thereafter withdrawn from, a pot 24 containing a bath 26 of molten solder. The pot 24 is displaced vertically, by way of a stepping motor (not shown), to and from the sample holder 22 so that at least part of the metallic portion 11 of the sample 12 held by the holder will be immersed into, and thereafter withdrawn from, the solder bath 26.

Figure 2:
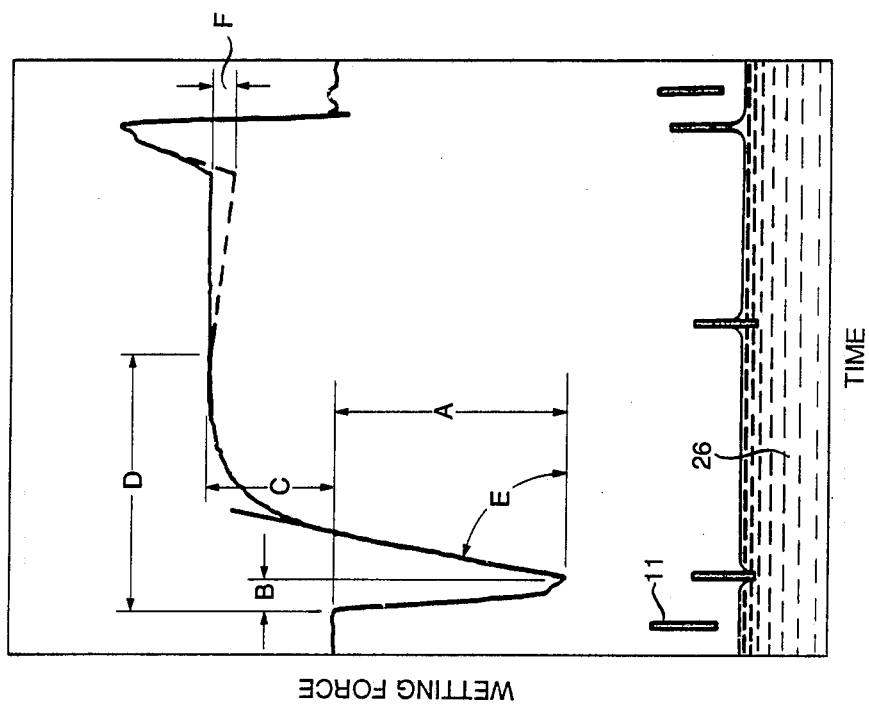
FIG. 2 shows a curve of the wetting force versus time as a sample is immersed in, and withdrawn from, a molten solder bath by the solderability tester of FIG. 1.

When immersed in the solder bath 26, the sample 12 experiences a wetting force as the solder wets the metallic portion 11 of the sample. Referring to FIG. 2, the upper plot shows the wetting force on the sample 12 during immersion into, and withdrawal from, the solder bath 26 over time. The lower plot represents the physical position of the metallic portion 11 of the sample relative to the solder bath 26 over time. The letters A, B, C, D, E and F in the upper plot of FIG. 2 represent: (A) the buoyancy force, (B) the time to begin wetting, (C) the maximum wetting force, (D) the time for maximum wetting, (E) the wetting rate (the tangent of the angle (E)), and (F) the amount of dewetting. By analyzing the upper plot of FIG. 2, the solderability of the metallic portion of the sample 12 held by the sample holder 22 can be accurately determined.

Figure 3:
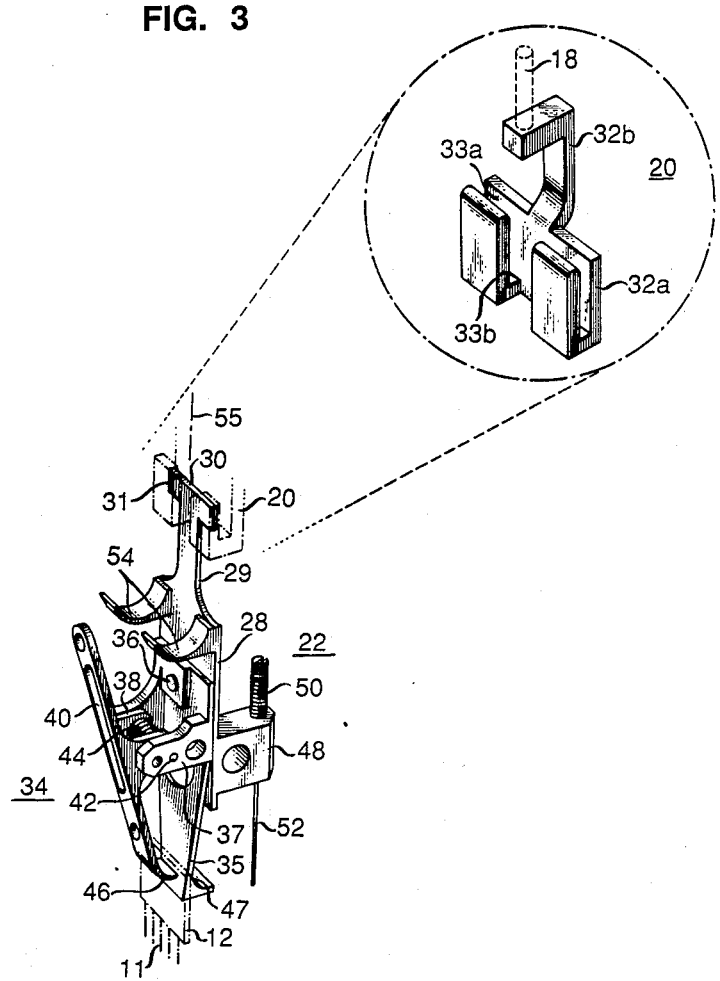
FIG. 3 is a perspective view of a first preferred embodiment of a solderability sample holder for the solderability tester of FIG. 1.
Figure 6:
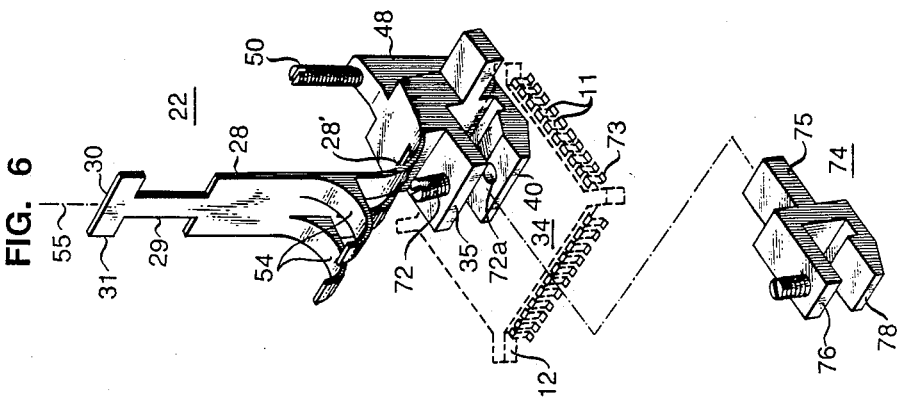
FIG. 6 is a perspective view of a third preferred embodiment of a solderability sample holder for the solderability tester of FIG. 1.
Figure 5:
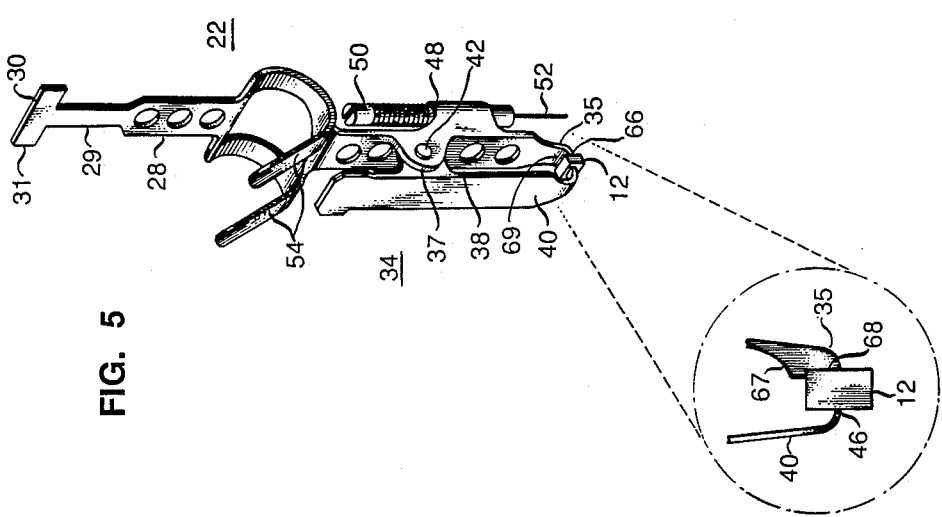
FIG. 5 is a perspective view of a second preferred embodiment of a solderability sample holder for the solderability tester of FIG. 1.

The prior art sample holder 22 of FIG. 1 incurs several disadvantages which are overcome, in large part, by a family of sample holders 22 constructed in accordance with the invention, individual members of which are shown in FIGS. 3, 5 and 6 and by an improved hanger 20 shown in FIG. 3. Referring to FIG. 3, there is shown a perspective view of a first sample holder 22 according to the invention for holding a moderately-sized sample 12, such as a soldered-on integrated circuit or a leaded discrete component. The sample holder 22 of FIG. 3 comprises an elongated flat beam 28 made from a lightweight metal, such as aluminum, which is resistant to the solder in the bath 26 of FIG. 1. The beam 28 has a pair of cut-outs 29 near its upper end 30, so that there exists a pair of oppositely extending "ears" 31 at the upper end of the beam. The oppositely extending ears 31 render the upper end 30 of the beam 28 "T"-shaped so that the holder 22 can be engaged by the hanger 20 of FIG. 1.

To assure more precise engagement of the sample holder 22 with the solderability tester 10 of FIG. 1, it was found desirable to replace the hanger 20 of FIG. 1 with an improved hanger 20 of FIG. 3. As best seen in FIG. 3, the improved hanger 20 comprises a block 32a, typically made from a metal such as aluminum, or the like. Integral with the block 32a is a right-angle hook 32b which extends upwardly from a lateral face on the block so as to overlie its top surface. A first slot 33a is precision machined longitudinally in the top surface of the block 32a while a second slot 33b is machined in the face of the block opposite the hook 32b to enable the ears 31 of the holder 22 to be engaged by the hanger 20. To facilitate easy disengagement of the upper end 30 of the beam 28 from the slots 33a and 33b in the block 32a, the lower edge of each ear 31 is radiused.

Referring to the sample holder 22 of FIG. 3, the beam 28 carries a clamping mechanism 34 distant from its upper end 30 for releasably engaging the sample 12. In FIG. 3, the clamping mechanism 34 comprises a first jaw 35, typically a flat strip, which is attached in face-to-face relationship with the beam 28 by a screw 36 so that a portion of the jaw depends below the beam. The jaw 35 has a pair of parallel, spaced-apart arms 37 which extend horizontally outward so as to lie outside of each of a pair of arms 38 extending horizontally outward in spaced parallelism from a second jaw 40, typically narrower in width than the first one. The arms 37 each engage opposite ends of a pin 42 rotatably journalled through the arms 38, thereby allowing the jaw 40 to pivot relative to the jaw 35.

Circumscribing the pin 42 is a coiled spring 44 which serves to bias the jaw 40 so that its lower end (the end below the arms 38) is urged towards the lower end of the jaw 35. The lowermost end of the jaw 40 is provided with an arcuate tip 46 which curves towards the jaw 35. When the upper end of the jaw 40 is biased so that the tip 46 is displaced away from jaw 35, the sample 12 can be inserted between the jaws. Upon release of the upper end of the jaw 40, the tip 46 at its lower end is now biased towards the jaw 35, so the sample 12 is captured between them. The curvature of the jaw tip 46 enables the sample 12, captured between the jaws 35 and 40, to be more precisely held than if the tip were not curved.

As can be observed in FIG. 3, the jaw 35 has a lip 47 at its lower end which extends horizontally outward in a direction opposite the jaw 40. The purpose of the lip 47 is to aid in alignment of the sample 12 as will be described later.

Integral with the beam 28 is a projection 48 which extends horizontally outward from the side of the beam opposite the jaw 35. A screw 50 is threaded vertically through an aperture (not shown) in the projection 48. Extending vertically downward from the base of the screw 50 below the projection 48 is a very narrow gauge (i.e., very fine) wire 52 made from a non-solder wetting metal, such as molybdenum. By threading the screw 50 into or out of the projection 48, the lower tip of the wire 52 can be raised to, or lowered from, the projection, respectively. Typically, the screw 50 has a very fine pitch (e.g., 40 threads per inch) to allow the distance between the tip of the wire 52 and the projection 48 to be set very precisely.

When the sample holder 22 of FIG. 3 is employed with the solderability tester 10 of FIG. 1, the lower tip of the wire 52 ultimately contacts the solder bath 26 as the pot 24 is raised towards the sample 12 to immerse the sample in the bath. The wire 52, which is electrically conductive but nonwettable by the solder 26, will make an electrical contact with the solder bath upon contact with it. Further, the beam 28 of the sample holder 22 is also electrically conductive, so that an electrical circuit between the sample holder and the solder bath 26 is completed once the tip of the wire 52 contacts the solder bath. By monitoring when the electrical circuit between the beam 28 and the bath 26 is completed, an indication can be had as to when the wire 52 contacts the bath, and hence, when the sample 12 has been immersed to a predetermined depth.

Referring to FIG. 3, a pair of dished, spaced-apart arms 54 extend horizontally outward from the beam 28 in a direction opposite the projection 48 so as to be at a height above the jaws 35 and 40. The arms 54 serve to carry opposite ends of a calibration weight (not shown). By placing a weight of known value on the arms 54 of the sample holder 22 at the outset of operation of the tester 10, the LVDT 14 of FIG. 1 will be subjected to a known force and can be appropriately calibrated. During actual operation of the tester 10, the weight is removed from the arms 54.

We discovered that when fabricating the sample holder 22 of FIG. 1, the location, shape and size of the jaws 35 and 40, the projection 48, and the arms 54 must chosen so that the sample holder remains balanced while the sample 12 is engaged. In other words, the beam 28 must have its longitudinal axis 55 substantially vertical during solderability testing. Significant unbalances in the sample holder 22 will likely cause the core 18 of the LVDT 14 of FIG. 1 to be unbalanced and given an erroneous measurement.

Figure 4:
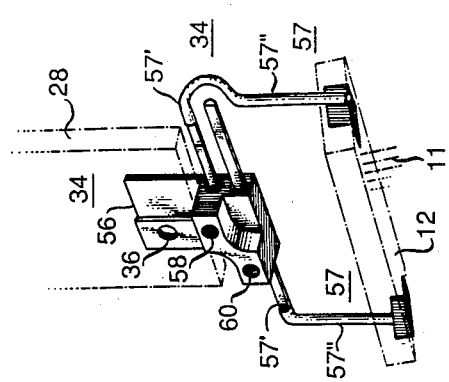
FIG. 4 is a perspective view of an alternate clamping mechanism for the sample holder of FIG. 3.

Referring to FIG. 4, there is shown an alternative clamping mechanism 34, capable of being substituted for the clamping mechanism on the sample holder 22 of FIG. 3, to enable the sample holder to engage a different class of samples 12, such as a dual-in-line package. The clamping mechanism 34 of FIG. 4 comprises a block 56 which is secured in face-to-face relationship with the beam 28 by the screw 36 in place of the jaw 35 of FIG. 2. The clamping mechanism 34 of FIG. 4 also includes a pair of generally "L"-shaped arms 57, which have a horizontal portion 57' and a vertical portion 57''. The horizontal portion 57' of each arm 57 extends into an opening in a separate one of the sides of the block 56 so the vertical portion 57'' of each arm is directed downwardly in spaced parallelism with the vertical portion of the other arm. A separate one of a set of set screws 58 and 60 is threaded into the front of the block 56 to bear against the horizontal portion 57' of each arm 57 extending into the block. By loosening each of the screws 58 and 60 and then displacing the horizontal portion 57' of each arm 57 into or out of the block 56, the spacing between the vertical portions 57'' of the arms can be adjusted.

At the lower end of the vertical portion 57'' of each arm 57 is a shelf 62 for supporting a separate one of the ends of a sample 12, such as a dual-in-line package, as seen in FIG. 4. The shelves 62 are each tilted at an angle so that when each of the ends of the dual-in-line package 12 is placed on a separate one of the shelves, the package itself is tilted such that one of its row of conductive members 11 lies below the other. Thus, the tips of the lower of the two rows of conductive members 11 on the package 12 are exposed first to the solder bath 26. By appropriately controlling the depth to which the conductive members 11 are immersed, it is possible to immerse a small portion of only the lower row of conductive members, allowing for a more accurate solderability measurement.

Referring now to FIG. 5, there is shown another sample holder 22 of the family of sample holders constructed in accordance with the invention. The sample holder 22 of FIG. 5 is generally comprised of the same elements as the sample holder of FIG. 3 and, therefore, like numbers have been used to reference like elements. However, the sample holder 22 of FIG. 5 does differ from that of FIG. 3 in several respects. For instance, the sample holder of FIG. 5 is specifically designed to engage a sample 12, typically a discrete surface-mounted resistor, capacitor or small outline transistor, which is much smaller in size than the sample engaged by the holder of FIG. 3.

To facilitate accurate solderability measurements of a very small sample 12, it is desirable to make the sample holder 22 of FIG. 5 as lightweight as possible. To this end, the beam 28 of the sample holder 22 of FIG. 5 is thinner, and is perforated, as compared to the beam of the sample holder of FIG. 3. In addition, the beam 28 of the sample holder 22 of FIG. 5 is much shorter, in that the beam effectively terminates at the arms 54, rather than extending a distance below them as in the case of the sample holder of FIG. 3.

The sample holder 22 of FIG. 5 also differs slightly from the holder of FIG. 3 in the construction of the clamping mechanism 34. Like the clamping mechanism 34 on the sample holder 22 of FIG. 3, the clamping mechanism on the sample holder of FIG. 5 is comprised of a first fixed jaw 35 and a second jaw 40 pivotally connected to, and spring-biased from, the first one. However, the first jaw 35 of the sample holder 22 of FIG. 5 is not releasably attached to the beam 28, as with the sample holder of FIG. 3, but is integral with, and depends from, the arms 54, which are themselves integral with and are thus carried by, the beam.

Further, the first jaw 35 of the sample holder 22 of FIG. 5 is perforated, and has a reduced-width, arcuate tip 66 at its lower end which curves toward, for abutment with, the arcuate tip 46 on the second jaw 40 which also has reduced width. As best seen in the inset portion of FIG. 5, the tip 66 has a horizontally projecting portion 67 facing the jaw 40. The projecting portion 67 has a rectangular cutout 68, sized to accommodate a very small, prismatically shaped sample 12, to firmly hold the sample in place. Referring to the main part of FIG. 5, a slot 69 is vertically cut into the projection 68 to allow an upwardly rising, conductive member (not shown) on the sample to seat itself in the projection.

Like the sample holder 22 of FIG. 3, the sample holder of FIG. 5 is provided with a depth-controlling screw 50 which has a fine wire 52 depending from it. The depth-controlling screw 50 on the sample holder 22 of FIG. 5 is threaded through a projection 48 which extends horizontally outward from the jaw 35 in a direction opposite to the arms 37 on the jaw. Like the depth-controlling screw 50 on the sample holder 22 of FIG. 3, the depth-controlling screw on the sample holder of FIG. 5 serves to control the depth of immersion of the sample 12 in the solder bath 26.

Referring now to FIG. 6, there is shown yet another sample holder 22 of the family of holders in accordance with the invention. The sample holder 22 of FIG. 6 shares the same basic structure as the sample holders of FIGS. 3 and 5, in that it is comprised of a beam 28 having a "T"-shaped upper end 30. Like the sample holders 22 of FIGS. 3 and 5, the holder of FIG. 6 has a pair of dished arms 54 extending horizontally outward from the beam 28 for carrying a calibration weight (not shown). Also, the beam 28 has a projection 48 extending horizontally therefrom in a direction opposite the arms for threadedly receiving a depth-controlling screw 50 provided with a depending wire (not shown).

The major difference in the construction of the sample holder 22 of FIG. 6 as compared to those of FIGS. 3 and 5 is in the construction of the clamping mechanism 34. The clamping mechanism 34 of the sample holder 22 of FIG. 6 is designed to clamp a relatively large sample 12, typically a plastic chip carrier as shown. Also, the clamping mechanism 34 of the sample holder 22 of FIG. 6 may advantageously engage a small piece of printed circuit board (not shown), hereinafter referred to as a "coupon."

To clamp these types of samples 12, the clamping mechanism 34 of FIG. 6 comprises a pair of planar jaws 35 and 40, each integral with, and extending laterally out from the beam 28 at an inclined angle so as to be in spaced parallelism one above the other, with a gap 70 therebetween. (As compared to the clamping mechanism 34 on the sample holder 22 of FIGS. 3 and 5, the clamping mechanism on the sample holder of FIG. 6 has its two jaws 35 and 40 fixed, rather than one jaw being fixed and the other being movable.) Referring to FIG. 6, a retaining screw 72 is perpendicularly threaded through the upper one of the jaws 34 and 40 to bear against the sample 12 inserted between the jaws. A clearance hole 72a is drilled through the lower one of the jaws.

An important aspect of the sample holder 22 of FIG. 6 is that a portion of the beam 28 lying just above the jaws 35 and 40 (indicated by the reference numeral 28' is made arcuate, so that the jaws are inclined relative to the longitudinal axis of the beam 55. In this way, the sample 12, when captured between the jaws 35 and 40, will be inclined or tilted relative to the beam's longitudinal axis 55.

There is a distinct advantage to inclining the sample 12, especially when the sample is a plastic leaded chip carrier as shown in FIG. 6. The conductive members 11 on present day chip carriers 12 typically have an arcuate toe 73 at their lowermost end. It is the toe 73 on each conductive member 11 that is actually soldered to a printed circuit board (not shown), and hence the solderability of the toe, rather than that of the entire conductive member, is of concern. When the plastic leaded chip carrier 12 is inclined so that one of its rows of conductive members 11 lies below the others, only the toes 73 on the conductive members in the lower row will be exposed to the solder bath 26 of FIG. 1 when the carrier is immersed into the solder bath to a predetermined depth. As a result, only the toes 73 in the lower row of conductive members 11 will be subjected to the wetting force of the solder in the bath 26, assuring a more accurate determination of their solderability. Exactly the same result is achieved for a leadless chip carrier package (not shown).

The ability of the sample holder 22 of FIG. 6 to hold the sample 12 at an inclined angle is also very important when the sample to be tested is a printed circuit board coupon (not shown). In the past, it has been difficult to obtain an accurate solderability test measurement of the metallized regions on a printed circuit board coupon by vertically dipping the board coupon in the solder bath 26 because of the large buoyancy effect of the coupon. However, with the sample holder 22 of FIG. 6, a printed circuit board coupon can be immersed at an angle so that the metallized regions on the coupon can be exposed while only exposing a small portion of the non-metallized part of the coupon, thus reducing the buoyancy force. In this way, a more accurate solderability measurement can be obtained.

A very unique advantage is obtained by using the sample holder 22 of FIG. 6 to engage a printed circuit board coupon (not shown) which is to be tested to ascertain the solderability of its metal-plated through holes. By holding the coupon so that its through holes are immersed at an inclined angle, we have found that a quantitative solderability measurement, similar to that shown in FIG. 2, can be obtained. The ability of prior art sample holders to hold printed circuit board coupons at an inclined angle in the same manner as the holder 22 of FIG. 6 has heretofore prevented an accurate assessment of the solderability of such coupons. Furthermore, the sample holder 22 of FIG. 6 may be used to hold a printed circuit board coupon containing metallized regions adapted for mounting surface-mounted components so that the solderability of such regions may be accurately assessed.

As shown in FIG. 6, associated with the sample holder 22 of that figure is an adapter 74 which may be utilized with the sample holder to permit it to engage a smaller sample 12 and hold it at an inclined angle. The adapter 72 comprises a tongue 75 adapted to fit between, and be engaged by, the jaws 35 and 40 of the sample holder 22 of FIG. 6. Integral with the tongue 62 is a pair of jaws 76 and 78 arranged one above the other in vertical, spaced-apart parallelism. A screw 80 is perpendicularly threaded through the upper one of the jaws 76 and 78 to bear against a sample (not shown) inserted between the jaws. The jaws 76 and 78 are each smaller in size than the jaws 35 and 40 of the sample holder and thus allow a smaller part to be more precisely engaged by the sample holder 22 of FIG. 6.

Figure 7:
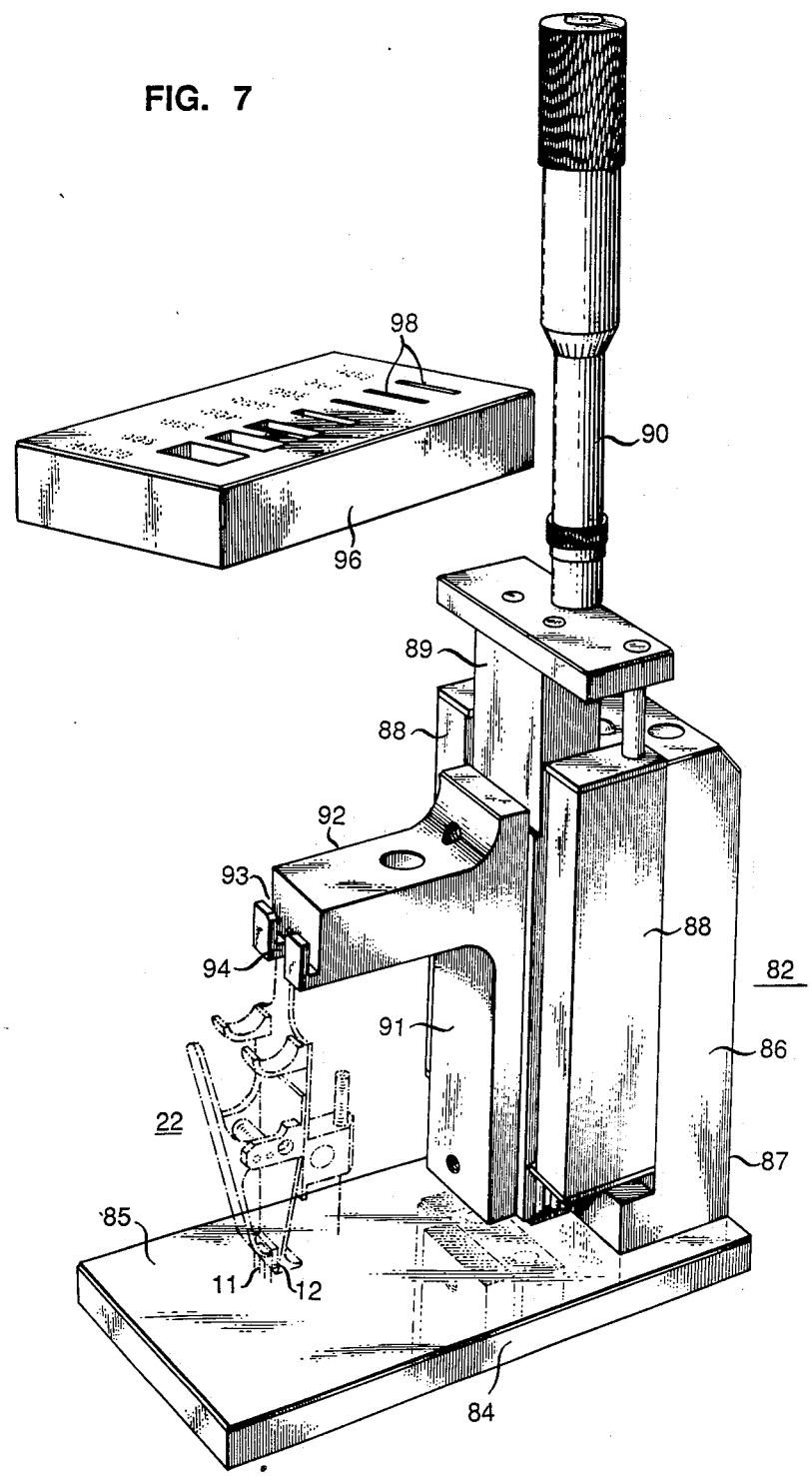
FIG. 7 is a perspective view of an alignment device for aligning a sample held by each of the sample holders of FIGS. 3, 5, and 6.

Referring to FIG. 7, there is shown an alignment device 82 for enabling the sample 12 carried by each of the sample holders 22 to be aligned such that the metallic portions 11 of the sample are properly positioned (i.e., at the same height). For purposes of illustration, the alignment device 82 is being shown with the sample holder 22 of FIG. 3 (illustrated in phantom). However, it should be understood that the sample holder 22 of FIGS. 5 and 6 could be substituted for the holder of FIG. 3.

The alignment device 82 comprises a base 84 having a highly polished reflective upper surface 85. A support 86 rises upwardly from the upper surface 85 of the base 86 such that a first side 87 of the support is substantially flush with an end of the base. Each of a pair of vertical columns 88 has a side affixed to the side of the support opposite the side 87 so that columns are in spaced-apart parallel at right angles to the support. A slide 89 is slidably mounted to the columns 88 for vertical movement. A lead screw (not shown) driven by a micrometer mechanism 90 is provided to precisely raise and lower the slide 89.

Attached to a face of the slide 89 is a member 91 which has a horizontally extending arm 92 which overlies a portion of the upper surface 85 of the base 84. Machined into the end of the arm 92 distant from the slide 89 is a pair of cross slots 93 and 94 which permit the arm to accommodate the "T"-shaped upper end 30 of one of the sample holders of FIGS. 3, 5 and 6 in exactly the same manner that the holder is engaged by the hanger 20 of FIGS. 1 and 3.

To align the sample 12 held by the sample holder 22, the "T"-shaped upper end 30 of the holder is secured to the end of the arm 92. Thereafter, the micrometer mechanism 90 is operated to lower the slide 91, and hence the sample holder 22, so that the metallic portions 11 of the sample 12 (i.e., the leads on the component engaged by the holder) are just touching the reflective surface 85 of the base 84. Misalignment of the sample 12 can be determined by observing whether all of the metallic portions 11 are touching the surface 85. If any of the metallic portions 11 are not touching the surface, then the sample (e.g., component) is misaligned. Observation of the alignment of the metallic portions 11 is greatly enhanced by virtue of the fact that the surface 86 is mirrored.

Also shown in FIG. 7 is an alignment block 96 which may be used in conjunction with, or independent of, the device 82 to align a sample held by the sample holder 22 of FIG. 3. The alignment block 96 is made from a block of metal, such as aluminum, and has a plurality of apertures 98 in its top surface of varying depths. When the sample holder 22 is inserted in a particular one of the apertures 98 such that the lip 47 contacts the upper surface of the block 96, the sample 12 will extend below the holder to the extent of the depth of the aperture. Thus, by seating the sample holder 22 in the proper aperture, the depth of the sample 12 below the holder can be established.

The foregoing discloses a family of sample holders 22 for holding different types of samples 12 for immersion in a solder bath 26 to test the solderability of the metallic portion 11 of the sample.

It is to be understood that the above-described embodiments are merely illustrative of the principles of the invention. Various modifications and changes may be made thereto by those skilled in the art which will embody the principles of the invention and fall within the spirit and scope thereof.

We claim:

1. Apparatus adapted for use with a solderability testing machine for holding a sample for immersion into a solder bath comprising:
   a beam having attachment means at one end adapted to releasably engage a solderability testing machine so that the beam hangs vertically;
   a clamping mechanism carried by the beam at a height below the attachment means and adapted to releasably engage a sample to hold it for immersion into a solder bath positioned therebeneath;
   a projection extending horizontally outwardly opposite the clamping mechanism; and
   a depth-controlling screw having a fine wire depending therefrom, the screw being threaded vertically through the projection so the wire depends below the beam for precisely controlling the depth of immersion of the sample in the solder bath thereberneath.

2. The appartus according to claim 1 wherein the clamping mechanism comprises:
   a first jaw depending vertically from the beam;
   a second jaw pivotally mounted to the first jaw so that the second jaw has its lower tip movable to and from the lower tip of the first jaw; and
   a spring for yieldably biasing the first jaw from the second jaw so that the lower tip of the second jaw is urged into abutment with the lower tip on the other jaw.

3. The apparatus according to claim 2 wherein the lower tip of each of the first and second jaws has a reduced width and curves toward the lower tip on the other jaw.

4. The apparatus according to claim 1 wherein the clamping mechanism comprises:
   a first and second fixed jaw extending outwardly at a downward inclined angle so that the jaws lie one above the other in spaced parallelism with a gap between them sized to accommodate at least a portion of a sample; and
   a retaining screw threaded through one of the first and second jaws to bear against a sample placed between them so that the sample and its metallic portion are held at a predetermined angle to limit the exposure of the metallic portion upon immersion in the solder bath.

5. The apparatus according to claim 1 wherein the clamping mechanism comprises:
   a block adapted for releasable attachment to the beam so as to be in face-to-face relationship therewith;
   a pair of "L"-shaped arms, each having a horizontal portion and a vertical portion, the horizontal portion of each arm extending into a separate one of a pair of opposed sides on the block so that the vertical portion of each arm extends downwardly, in spaced parallelism with the vertical portion of the other arm;
   a shelf carried by the vertical portion of each arm at its lowermost end, each shelf being inclined with respect to the vertical portion of its corresponding arm and adapted to support a separate one of the ends of a sample so the sample, when supported by the shelves, has its metallic portion inclined.

6. The apparatus according to claim 1 wherein the attachment means comprises a pair of ears extending outwardly from the beam in opposite directions and wherein the sample holder further includes a hanger for releasably attaching the sample holder to the solderability testing machine, the hanger including a block having an upwardly rising hook for attachment to the solderability testing machine and a pair of cross slots cut into the top and side of the block, respectively, to accommodate the ears of the sample holder.

7. A kit of sample holders for use with a solderability testing machine, each sample holder adapted for releasable attachment to the solderability tester to releasably engage a sample for immersion into a solder bath comprising:
- a plurality of sample holders, each comprised of:
- a beam having attachment means at one end adapted to releasably engage a solderability testing machine so that the beam hangs vertically;
- a clamping mechanism carried by the beam at a height below the attachment means and adapted to releasably engage a sample to hold it for immersion into a solder bath positioned therebeneath;
- a projection extending horizontally outwardly opposite the clamping mechanism;
- a depth-controlling screw threaded vertically through the projection so as to depend below the beam for precisely controlling the immersion of the sample held by the sample holder into the solder bath therebeneath;
- a pair of spaced-apart arms carried to the beam at a height above the clamping mechanism and extending outwardly in a direction opposite the projection for holding a calibration weight, the clamping mechanism of each sample differing from that of the other holders to enable each holder to hold a different type of sample; and
- an alignment device adapted to engage each of the sample holders so that a sample held thereby can be inspected to determine if the sample is properly aligned.

8. The kit according to claim 7 wherein a first one of the sample holders has a clamping mechanism comprised of:
- a first jaw depending vertically from the beam;
- a second jaw pivotally mounted to the first jaw so that the second jaw has its lower tip movable to and from the lower tip of the first jaw; and
- a spring for yieldably biasing the first jaw from the second jaw so that the lower tip of the second jaw is urged into abutment with the lower tip of the first jaw.

9. The kit according to claim 7 wherein a second one of the sample holders has a clamping mechanism comprised of:
- a first jaw depending vertically from the beam;
- a second jaw pivotally mounted to the first jaw so that the second jaw has its lower tip movable to and from the lower tip of the first jaw;
- a spring for yieldably biasing the first jaw from the second jaw so that the lower tip of the second jaw is urged into abutment with the lower tip of the first jaw; and
- the lower tip of each of the first and second jaws has a reduced width and curves toward the lower tip on the other jaw.

10. The kit according to claim 7 wherein a third one of the sample holders has a clamping mechanism comprised of:
- a first and second fixed jaw extending outwardly at a downward inclined angle so that the jaws lie one above the other in spaced parallelism with a gap between them sized to accommodate at least a portion of a sample; and
- a retaining screw threaded through one of the first and second jaws to bear against a sample placed between them so that the sample and its metallic portion are held at a predetermined angle to limit the exposure of the metallic portion upon immersion in the solder bath.

11. The kit according to claim 7 wherein the alignment device comprises:
- a base having a reflective upper surface;
- a support rising upwardly from the mirrored surface on the base;
- a slide slidably mounted for vertical movement along the support;
- an arm extending outwardly from the slide so as to overlie at least a portion of the mirrored surface on the base;
- means at the end of the arm distant from the slide adapted to releasably engage a sample holder so that the holder hangs vertically from the arm; and
- means for precisely displacing the slide along the column so that the sample holder may be precisely raised and lowered to position the sample held thereby proximate the mirrored surface to permit observation of whether the sample is properly aligned.

* * * * *